United States Patent [19]

Wevers et al.

[11] 4,444,181

[45] Apr. 24, 1984

[54] BONE CLIP

[75] Inventors: Henk S. Wevers; Charles Sorbie, both of Kingston; Gerald A. B. Saunders, Bath, all of Canada

[73] Assignee: Queen's University at Kingston, Kingston, Canada

[21] Appl. No.: 312,939

[22] Filed: Oct. 20, 1981

[30] Foreign Application Priority Data

Nov. 10, 1980 [CA] Canada .................................. 364395

[51] Int. Cl.³ .............................................. A61F 5/04
[52] U.S. Cl. .................................. 128/92 D; 128/92 B
[58] Field of Search ...................... 128/92 B, 335, 337, 128/92 EA, 92 R, 336, 92 D

[56] References Cited

U.S. PATENT DOCUMENTS

| 3,150,379 | 9/1964 | Brown | 128/335 |
| 3,203,220 | 8/1965 | Kaepernik | 128/335 |
| 3,807,394 | 4/1974 | Attenborough | 128/92 B |
| 3,825,010 | 7/1974 | McDonald | 128/335 |
| 4,170,990 | 10/1979 | Baumgart et al. | 128/92 B |
| 4,317,451 | 3/1982 | Cerwin et al. | 128/335 |

FOREIGN PATENT DOCUMENTS 910578 3/1954 Fed. Rep. of Germany ...... 128/335

OTHER PUBLICATIONS

Bickham's *Operative Surgery*, 1924, pp. 365 and others.

*Primary Examiner*—C. Fred Rosenbaum
*Assistant Examiner*—C. W. Shedd
*Attorney, Agent, or Firm*—Richard J. Hicks; Stanley E. Johnson

[57] ABSTRACT

A bone clip for surgical repair of bones in vivo, having a body and depending legs at each end thereof and perpendicular thereto. Means are provided to draw the legs inwardly towards each other after insertion into the bone so as to draw the bone ends together under a preselected pressure.

3 Claims, 9 Drawing Figures

BONE CLIP

This invention relates to a method and apparatus for the surgical repair of bones in vivo. More particularly this invention relates to a bone clip for securing bones under a selected compressive force.

It is, of course, well known that a surgeon may reduce a fracture in a limb, set the ends of the bone in the desired orientation and hold them in that orientation by means of an externally applied splint or cast. It is also known to secure the broken ends of a bone by means of screws, pins and staples surgically implanted directly into the bone. Such screws, pins and staples must of course be fabricated in a material, such as the alloy VITALLIUM ®, which is tolerated by the body as they may be implanted permanently in the body. While all such devices are satisfactory for their particular functions there nevertheless remains a need for further improvements in prostheses for use in particular applications. For example, diseases such as arthritis can cause bone deformities particularly in small bones such as the fingers. Such deformities may be corrected surgically by removing a wedge shaped piece of bone from one side of the finger and straightening the bone by drawing the ends thereof together. The ends must then be held under pressure at least until they reunite. While a simple staple will perform the function of holding the bones in position it is not effective to draw the ends of the bone together.

It is, therefore, an object of the present invention to provide a bone clip which not only retains bone orientation but which is capable of applying a preselected pressure thereon.

Thus, by one aspect of this invention there is provided a bone clip comprising: a body member; a leg member at each longitudinal end of said body member and substantially perpendicular thereto; and means to draw at least a portion of each said leg member towards the other said leg member so as to secure said bone clip in a bone.

The invention will be described in more detail hereinafter with reference to the drawings in which.

Figure 2:
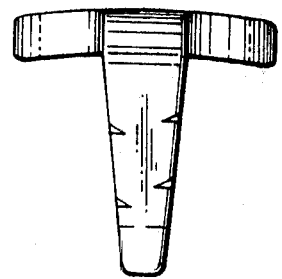
FIG. 2 is a side view of the clip of FIG. 1.
Figure 3:
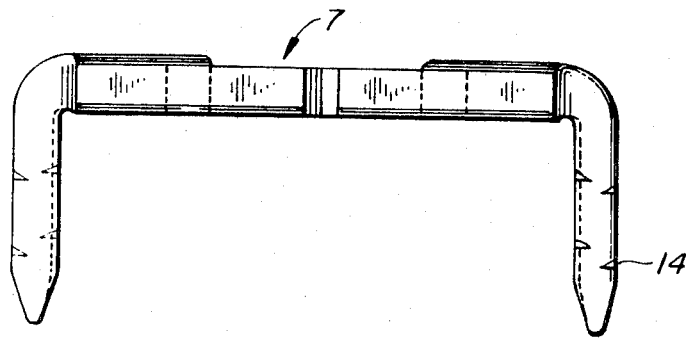
FIG. 3 is an end view of the clip of FIG. 1.
Figure 1:
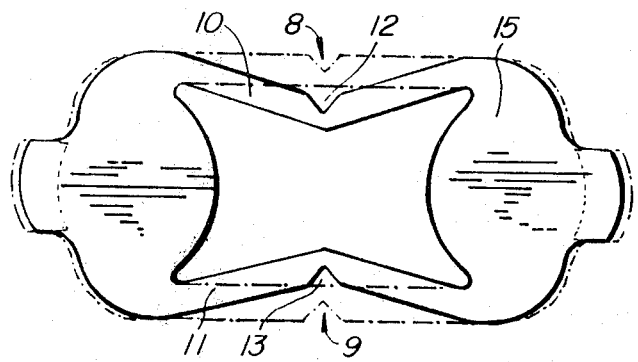
FIG. 1 is a plan view of one embodiment of a clip of the present invention.
Figure 4A:
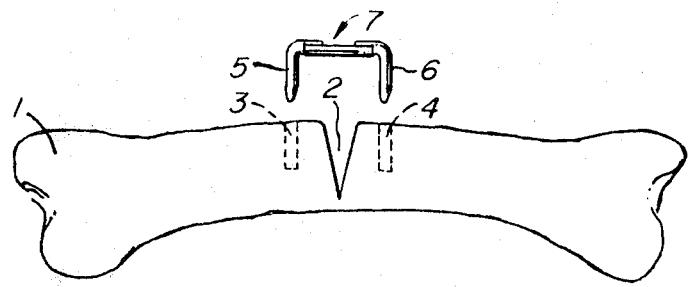
FIG. 4(a) is a sketch showing a clip preparatory to installation in a bone.
Figure 4B:
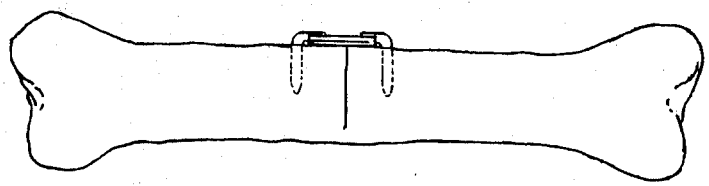
FIG. 4(b) is a sketch showing a clip as installed in a bone.

Turning firstly to FIG. 4(a), there is depicted a deformed bone, such as a digital bone 1 which is to be surgically straightened by drawing the sides of a V-notch 2, cut into the bone, together. Pin holes 3, 4 are drilled into the bone on each side of notch 2 to receive the depending legs 5, 6 respectively of a bone clip 7 having a substantially rectangularly shaped hollow body member 15. After insertion of clip 7, the surgeon takes a crimping device such as a pair of pliers and applies a compressive force as shown by arrows 8, 9 in FIG. 1 on the marginal side edges or arms 10, 11 of the body member 15, so as to move the side edges from the position shown in chain dot to the position shown in solid lines, and thereby drawing the depending legs 5, 6 inwardly towards each other. Notches 12, 13 are provided in side arms 10, 11 respectively to facilitate bending or deformation thereof. FIGS. 2 and 3 show side and end views of the clip 7 and further illustrate notches 14 in the depending legs which are designed to facilitate gripping in the bone structure. Clip 7 may be fabricated from sheet material or may be produced by a conventional casting or powder metallurgical process.

Figure 5:
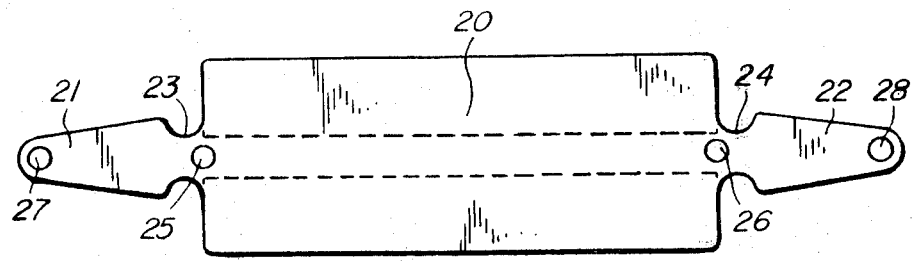
FIG. 5 is a plan view of an alternative embodiment of the invention.
Figure 6:
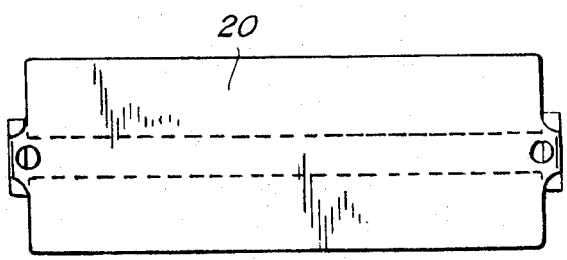
FIG. 6 is a plan view, similar to FIG. 5, showing the legs in operative position.
Figure 7:
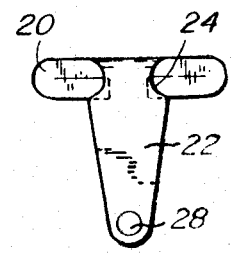
FIG. 7 is an end view of the embodiment of FIG. 6.
Figure 8:
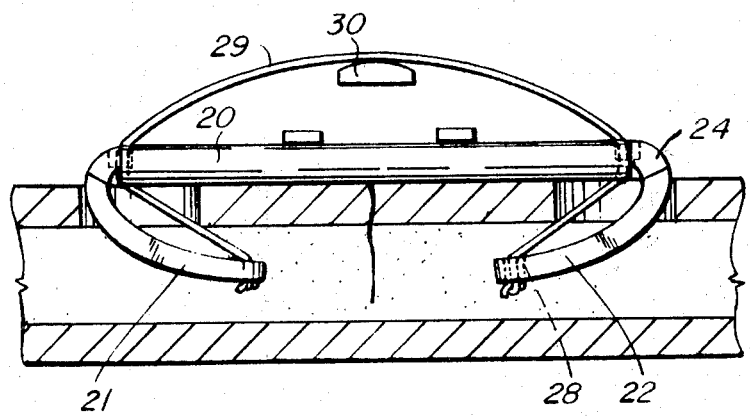
FIG. 8 shows the embodiment of FIG. 5 as installed in a bone.

It will, of course, be appreciated that FIGS. 1–4 merely illustrate one preferred embodiment of the invention as there are numerous ways in which the essential feature thereof, namely means to draw the downwardly depending legs of the clip or staple 7 inwardly, may be achieved. One such alternative means is illustrated in FIGS. 5–8. A rectangular clip body 20 is provided with projecting legs 21, 22 at opposite ends thereof which are connected to the body 20 by weakened portions 23, 24 respectively. Body 20 and legs 21, 22 may be conveniently fabricated from sheet material. As shown in FIGS. 5, 6 and 7 the marginal side edges are turned over to provide additional strength to the body. Holes 25 and 26 are drilled in body 20 adjacent weakened portions 23, 24 respectively, and holes 27, 28 are drilled adjacent the outward ends of legs 21, 22 respectively. The legs 21, 22 are bent about the weakened portions 23, 24 to a position substantially perpendicular to body 20, as shown more clearly in FIGS. 6 and 7. The clip is now in position for insertion into bone holes 3, 4 as described with reference to FIG. 4(a), before doing so, however, a piece of wire 29, usually of stainless steel, is secured to leg 21 through hole 27 and passed along the inner wall thereof, through hole 25 and over the upper surface of body 20, through hole 26 and secured to leg 22 through hole 28. After insertion into the bone as shown in FIG. 8 a pair of pliers or other expanding tool 30 is inserted between wire 29 and body 20 as shown in FIG. 8 and the wire is pulled up, thereby causing legs 21, 22 to be drawn inwardly towards each other and thus becoming securely fastened in the bone as shown in FIG. 8, or through the bone (not shown). The wire 29 may be cut off adjacent holes 25, 26 if desired. An advantage of the embodiment shown in FIGS. 5–8 is that it can be used in or completely through a selected bone and furthermore may be anchored permanently in the bone, if desired.

While this invention has been described with reference to the straightening of bones such as the phalanges, or phalanxes of the hand, it will be appreciated that the bone clip of the present invention can be used for other purposes including:

1. Foot bones (wedge osteotomy);
2. Triple arthrodesis (correction of club foot by taking wedges out of the ankle bones and drawing the remaining part together);
3. Fractures of all flat bones such as pelvis and craneotomies and craneoplasties);
4. Fractures of the sternum (breastbone) or after sternum splitting and incision for cardiac surgery;
5. Fractures of ribs;
6. Fractures of upper and lower limbs, e.g. distal humerus, metacarpals and phalanges, the fibula and the foot bones.

We claim:

1. A one piece endoprosthetic bone clip for joining bones in vivo under a selected compressive force, comprising:

an elongated metallic body member having an elongated slot means in a central portion thereof and having coplanar, unilaterally extending single legs at each longitudinal end thereof; said legs being formed unitarily with and extending substantially perpendicular to said body member; said legs being adapted for insertion into respective predrilled holes in said bones being joined;

said body member including arm means, contiguous said slot means, for being plastically deformed in a plane perpendicular to the plane of said legs, so as to draw said legs towards each other in parallel relation, imparting said selected force, and thereby joining said bones.

2. A bone clip as claimed in claim 1 wherein said arm means include notch means intermediate the ends to facilitate deformation thereof.

3. An endoprosthetic bone clip as claimed in claim 1 wherein said legs include notch means to facilitate gripping in said bones.

* * * * *